US009823218B2

(12) United States Patent
Klootwijk et al.

(10) Patent No.: US 9,823,218 B2
(45) Date of Patent: Nov. 21, 2017

(54) INTEGRATED CIRCUIT WITH NANOWIRE CHEMFET-SENSORS, SENSING APPARATUS, MEASURING METHOD AND MANUFACTURING METHOD

(71) Applicant: KONINKLIJKE PHILIPS N.V., Eindhoven (NL)

(72) Inventors: Johan Hendrik Klootwijk, Eindhoven (NL); Marleen Mescher, Eindhoven (NL); Manuel Eduardo Alarcon-Rivero, Eindhoven (NL); Nico Maris Adriaan De Wild, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/435,190

(22) PCT Filed: Oct. 7, 2013

(86) PCT No.: PCT/IB2013/059173
§ 371 (c)(1),
(2) Date: Apr. 13, 2015

(87) PCT Pub. No.: WO2014/060896
PCT Pub. Date: Apr. 24, 2014

(65) Prior Publication Data
US 2015/0276668 A1 Oct. 1, 2015

Related U.S. Application Data

(60) Provisional application No. 61/714,352, filed on Oct. 16, 2012.

(51) Int. Cl.
*G01N 27/02* (2006.01)
*G01N 27/04* (2006.01)
(Continued)

(52) U.S. Cl.
CPC ..... *G01N 27/4148* (2013.01); *G01N 27/4145* (2013.01); *G01N 27/4146* (2013.01)

(58) Field of Classification Search
CPC ........... G01N 27/4145; G01N 27/4146; G01N 27/4148
See application file for complete search history.

(56) References Cited

U.S. PATENT DOCUMENTS

| 4,820,973 A | 4/1989 | Alvarez |
| 2004/0136866 A1 | 7/2004 | Pontis |

(Continued)

FOREIGN PATENT DOCUMENTS

| EP | 2362219 A1 | 8/2011 |
| GB | 2294808 A | 5/1996 |
| JP | 2008525822 A | 7/2008 |

OTHER PUBLICATIONS

Yoo S.K. et al, "Subthreshold operation of Schottky barrier silicon nanowire FET for highly sensitive pH sensing", Electronic Letters, TEH Institution of Engineering and Technology, vol. 46, No. 21, Oct. 14, 2010.

(Continued)

*Primary Examiner* — Robert Eom

(57) ABSTRACT

Integrated circuit (100) comprising a semiconductor substrate (110); an insulating layer (120) over said substrate; an first transistor (140) on said insulating layer, said first transistor comprising an exposed channel region (146) in between a source region (142*a*, 142*b*) and a drain region (144); and a voltage waveform generator (150) conductively coupled to the semiconductor substrate for providing the first transistor with a bias voltage during a signal acquisition period, wherein the voltage waveform generator is arranged to generate an alternating bias voltage waveform (300) comprising a periodically increasing amplitude. A sensing (Continued)

apparatus including such an integrated circuit and a sensing method using such an integrated circuit are also disclosed.

13 Claims, 6 Drawing Sheets

(51) Int. Cl.
*G01N 27/12* (2006.01)
*G01N 27/414* (2006.01)

(56) References Cited

U.S. PATENT DOCUMENTS

| | | | |
|---|---|---|---|
| 2006/0246497 A1* | 11/2006 | Huang | G01N 27/4146 435/6.14 |
| 2006/0263255 A1 | 11/2006 | Han | |
| 2006/0270053 A1 | 11/2006 | Tilak | |
| 2008/0093226 A1 | 4/2008 | Briman | |

OTHER PUBLICATIONS

M. Mattmann, C Roman, T Helbling, D Bechstein / "Pulsed gate sweep strategies for hysteresis reduction in arbon anatube transistors for low concentration No2 gas detection", Nanotechnology, IOP Publishing, 2010, May 7, vol. 21, No. 18, 185501.

\* cited by examiner

INTEGRATED CIRCUIT WITH NANOWIRE CHEMFET-SENSORS, SENSING APPARATUS, MEASURING METHOD AND MANUFACTURING METHOD

This application is the U.S. National Phase application under 35 U.S.C. §371 of International Application No. PCT/IB2013/059173, filed on Oct. 7, 2013, which claims the benefit of U.S. Provisional Application No. 61/714,352 filed on Oct. 16, 2012. These applications are hereby incorporated by reference herein.

FIELD OF THE INVENTION

The present invention relates to an integrated circuit comprising a semiconductor substrate; an insulating layer over said substrate; an analyte first transistorfirst transistor on said insulating layer, said first transistorfirst transistor comprising an exposed channel region in between a source region and a drain region; and a voltage waveform generator conductively coupled to the semiconductor substrate for providing the first transistorfirst transistor with a bias voltage during a signal acquisition period.

The present invention further relates to a sensing apparatus including such an IC.

The present invention yet further relates to a method of measuring an analyte of interest in a medium using such an IC.

BACKGROUND OF THE INVENTION

The on-going miniaturization of semiconductor technology has enabled a remarkable diversification of functionality embedded in semiconductor devices such as integrated circuits (ICs), which in some cases has led to the provision of near-holistic solutions on a single device. For instance, semiconductor device miniaturization has led to the integration of one or more sensors into a single semiconductor device, and the deployment of such devices can be seen in widely different technical areas, e.g. automotive applications, healthcare applications, industrial gas flue monitoring and so on.

One of the major challenges in providing sensing functionality on an electronic device such as an IC is to ensure that the semiconductor device can be produced in an economically feasible manner. This is for instance a particular challenge when sensing elements of sub-micron dimensions, e.g. nano-elements such as nanowire-based transistors, are to be integrated in the semiconductor device, as it is not at all straightforward to manufacture such nano-elements using processing steps that are compatible with the manufacturing process of the overall semiconductor device. Hence, the integration of such dedicated elements can lead to a significant increase in the complexity of the manufacturing process of the semiconductor device, thereby significantly increasing the cost of such devices.

A particular problem in this respect is that when the sensing medium is a fluid, e.g. a liquid or gas, the sensor arrangement usually requires the presence of a reference sensor or electrode to compensate for sensor drift, i.e. the time-varying response of a sensor to an analyte of interest, which for instance can be caused by the gradual build-up of contaminants on the sensor surface. Such build-up for instance occurs when the first transistorfirst transistor is biased with a constant voltage, thereby causing a potential difference between the medium and the exposed channel region, which can cause accumulation of charged particles on the sensor surface, which in turn can cause a shift in the threshold voltage $V_{th}$ of the first transistorfirst transistor.

An example of such an arrangement is disclosed in US 2004/0136866 A1, in which a reference electrode is placed into contact with a fluid to be analysed in order to control the potential of the solution relative to the semiconductor nanowire sensing element.

However, the inclusion of a reference sensor or electrode can further complicate the design of the sensor arrangement, which therefore can further increase the cost of the electronic device. Moreover, the surface of the reference electrode itself can also be prone to fouling, in which case the sensor readings can become unreliable.

EP 2 362 219 A1 discloses a method of performing a measurement with a sensor having a sensing surface and at least one capture molecule attached to the sensing surface for forming a binding pair with an analyte of interest, the binding pair having a flexible spatial orientation, the method comprising capturing the analyte of interest with the capture molecule, thereby forming the binding pair in an initial spatial orientation; applying a first electromagnetic force to the sensing surface to alter the spatial orientation of the binding pair; and performing a sensor measurement with the binding pair in the altered spatial orientation. Consequently, a sensor output signal is produced that is modulated with the EMF-induced conformational changes in the binding pair, such that signal contributions from contaminants, which typically do not exhibit the EMF-induced modulation are effectively filtered out.

SUMMARY OF THE INVENTION

The present invention seeks to provide an IC according to the opening paragraph in which the need for a separate reference electrode is avoided.

The present invention further seeks to provide a sensing apparatus including such an IC.

The present invention yet further seeks to provide a method of measuring an analyte of interest using such an IC.

The invention is defined by the independent claims. The dependent claims define advantageous embodiments.

In accordance with an aspect of the present invention, there is provided an integrated circuit as defined in the invention. The first transistor is particularly useful for sensing of an analyte of interest. The first transistor can be an analyte sensing transistor.

The present invention is based on the realization that by providing an IC having a first transistor with an affinity for a particular analyte of interest, e.g. because the channel region of the transistor is appropriately functionalized with e.g. a functionalization layer, the negative influence of contaminants on the sensing signal can be largely avoided by the application of a bias voltage waveform that periodically attracts and repels such contaminants, e.g. ions, without the need to extract a modulated component from the sensor signal acquired during the application of the bias voltage waveform. Instead, it has surprisingly been found by periodically increasing the amplitude of at least one part of the waveform, e.g. the positive part and/or the negative part, applied to the back gate of the first transistor, an accurate analyte measurement can be performed with the first transistor by deriving the analyte contribution from the acquired signal, e.g. from its inclination and/or from its $V_{th}$. An additional advantage of using such a voltage waveform over the provision of a constant back bias voltage is that the drain-source current of the transistor becomes insensitive to the bias voltage that is applied to the transistor.

The IC may further comprise a signal processor conductively coupled to the analyte first transistor and arranged to derive an analyte measurement from the analyte first transistor signal acquired during said signal acquisition period. Alternatively, such a signal processor may be provided off-chip.

In an embodiment, the bias voltage waveform has a time-averaged potential of zero, e.g. by providing a bias voltage waveform that (symmetrically) oscillates around a zero value. This has the advantage that charged particles, e.g. ions, cannot effectively bind to the channel region of the first transistor unless they have a special affinity with the channel region, e.g. in the case of a suitable binding layer on the channel region, because the time averaged bias potential does not yield an attractive force for such particles.

Alternatively, the voltage sweep comprises a plurality of alternating positive and negative voltage pulses, wherein only one of the positive voltage pulses and negative voltage pulses exhibits a periodically increasing amplitude. For instance, only the maximum, i.e. the positive, voltage component of the sweep may be gradually increased from an initial value to a final value, whereas the minimum or negative voltage amplitude is kept at a constant value in each of these periods, thus yielding a positive potential that increases in a number of steps and which is alternated with a fixed negative potential. It has been surprisingly found that such a potential is particularly effective in preventing the accumulation of charged contaminants at the surface of the channel region, whilst at the same time allowing the accumulation of charged particles or molecules of interest due to the additional stabilization with the binding layer on the channel region. This is because the positive part of the voltage waveform acts as a pulsed waveform with an increasing intensity over time, whilst the negative part of the waveform ensures that the average potential over the period during which the voltage waveform is applied remains zero.

In a preferred embodiment, the channel region comprises a nanowire or a nanotube, such as a silicon nanowire or a carbon nanotube. Because such nanowires or nanotubes can be manufactured in a CMOS compatible manner and at submicron dimensions, an array of transistors having a high transistor density can be manufactured in a low-cost manner in a CMOS process.

The channel region may be covered by an oxide film, e.g. by partial oxidation of the channel region, such that the oxide film acts as a gate oxide. The channel region may further be covered by a binding layer for functionalizing the channel region such that it predominantly binds a particular analyte of interest, e.g. a biomolecule such as DNA, living organisms such as bacteria or viruses, a particular type of ion, a particular type of (charged) molecule and so on.

In accordance with another aspect of the present invention, there is provided a sensing apparatus as defined in the invention. Such a sensing apparatus benefits from a reliable and accurate determination of the presence and/or concentration of an analyte of interest in the sample compartment, e.g. a fluid flowing through a flow cell comprising the exposed analyte first transistor, without the need for a separate reference electrode.

In accordance with yet another embodiment of the present invention, there is provided a method of measuring an analyte of interest in a medium as defined in the invention. This way, the negative influence of contaminants on the sensing signal can be largely avoided by the application of a bias voltage waveform that periodically attracts and repels such contaminants, e.g. ions, without the need to extract a modulated component from the sensor signal acquired during the application of the bias voltage waveform as previously explained.

The biasing step may comprises biasing the analyte first transistor with a bias voltage waveform having a time-averaged zero potential to minimize the risk of charged contaminants adhering to the exposed channel region surface. To this end, the bias voltage waveform may (symmetrically) alternate around a zero value.

In another embodiment, the bias voltage waveform comprises a plurality of alternating positive and negative voltage pulses, wherein only one of the positive voltage pulses and negative voltage pulses exhibits the periodically increasing amplitude, as this waveform shape has been found particularly suitable to repel charge bearing contaminants from the sensing surface whilst at the same time allowing the binding of charged analytes of interest as previously explained.

BRIEF DESCRIPTION OF THE EMBODIMENTS

Embodiments of the invention are described in more detail and by way of non-limiting examples with reference to the accompanying drawings, wherein FIG. 1 schematically depicts an aspect of an IC according to an embodiment of the present invention;

Figure 7:
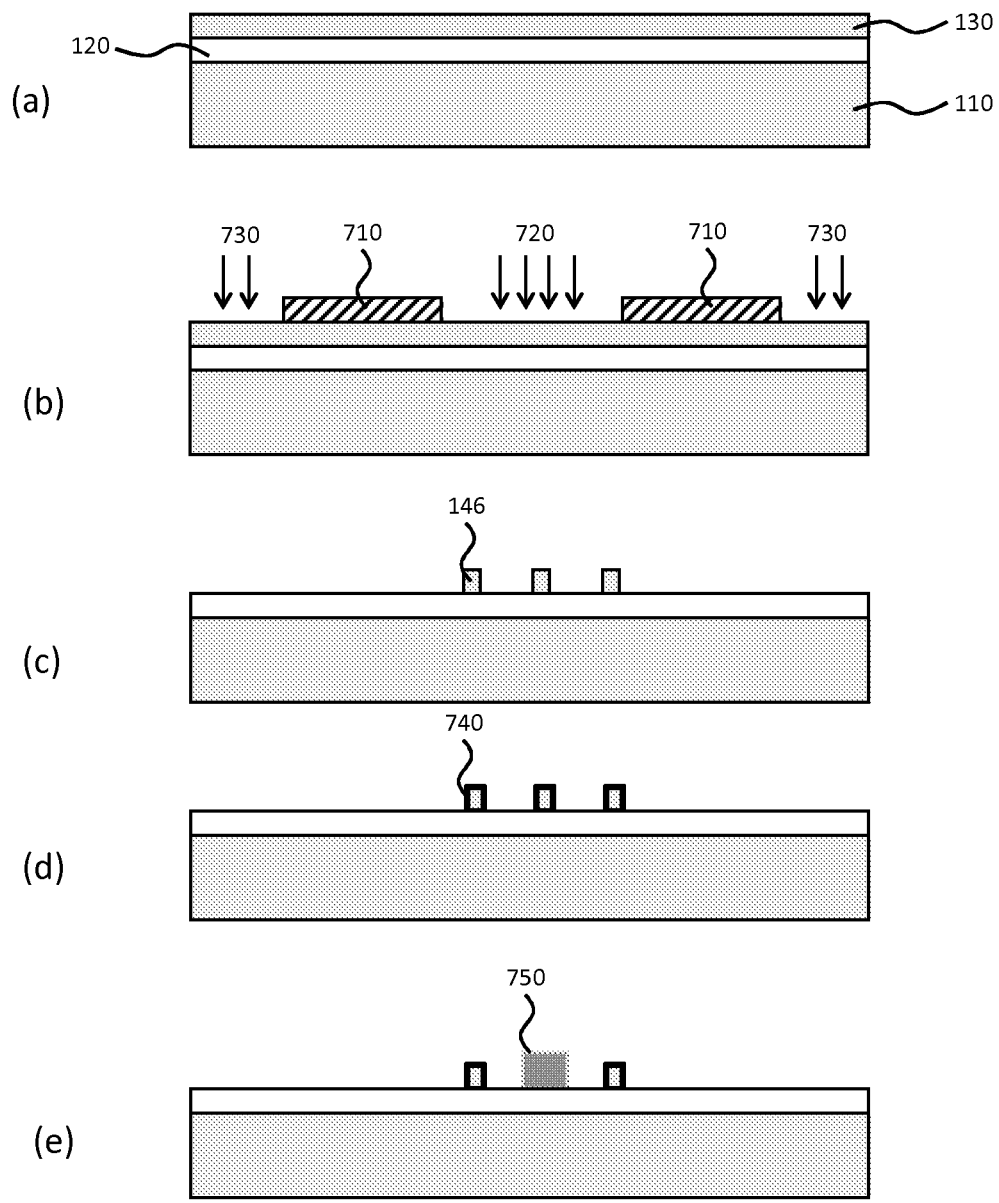
Figure 8:
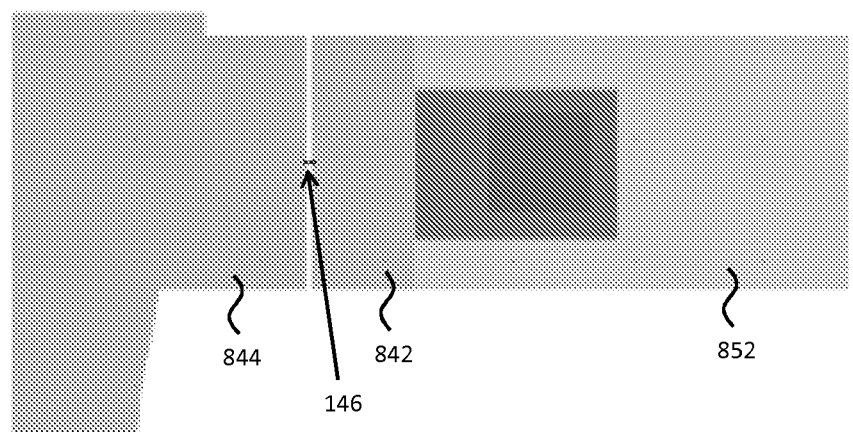

FIG. 7A-E schematically depict an embodiment of a method of manufacturing the IC of the present invention; and FIG. 8 schematically depicts a further aspect of an IC according to an embodiment of the present invention.

DETAILED DESCRIPTION OF THE DRAWINGS

It should be understood that the Figs are merely schematic and are not drawn to scale. It should also be understood that the same reference numerals are used throughout the Figs to indicate the same or similar parts.

Figure 1:
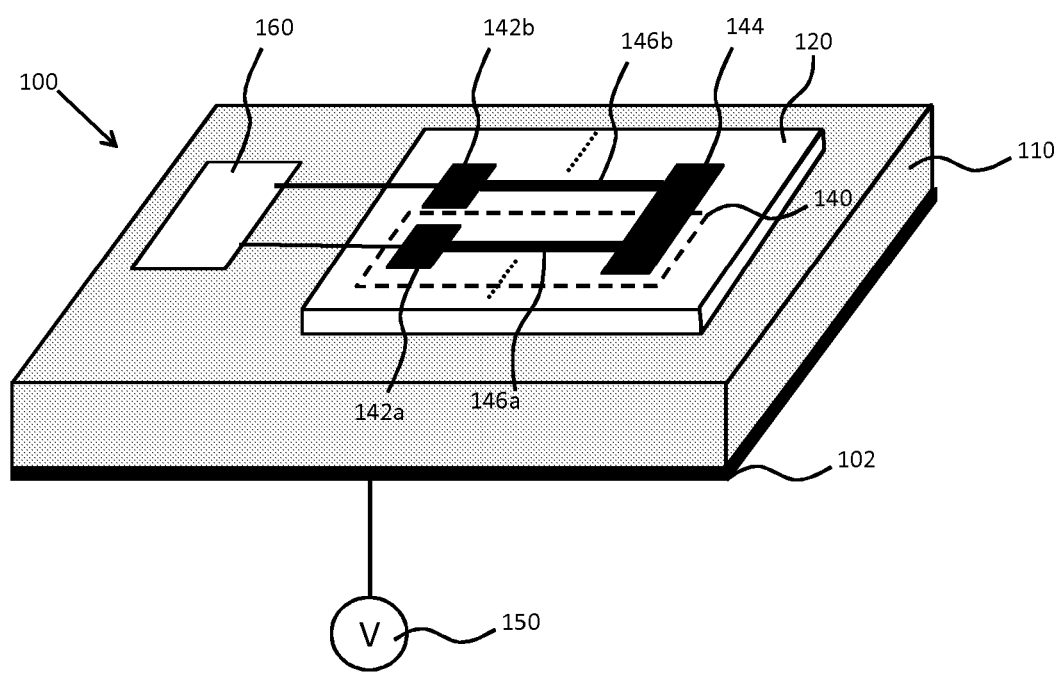

The IC 100 of FIG. 1 comprises a silicon substrate 110, a patterned buried oxide layer 120 and a plurality of sensing field effect transistors 140 that have a nanostructure such as a silicon nanowire or a carbon nanotube as channel region. Two first transistors 140 with respective nanowires 140a and 140b are shown, but it should be understood that the IC 100 may comprise a much larger number of such transistors, which preferably have channel regions arranged adjacent to each other in an array.

In FIG. 1, the first channel region 146a extends between a source region 142a and a drain region 144, whereas the second channel region 146b extends between a source region 142b and the drain region 144. The first channel region 146a and the second channel region 146b thus share a drain region for providing the nanowire channel regions with a common drive current, with the individual source regions 142a and 142b allowing measurement of the current induced through individual nanowires. It should be understood that this arrangement is by way of non-limiting example only; it is equally feasible for the first transistors 140 to share a source region and have individual drain regions, or to have individual source and drain regions, although the latter complicates the manufacturability of the IC 100 due to the fact that a larger number of contacts to these individual regions has to be provided.

In the context of the present invention, a nanowire is a conductive or semiconductive structure having a cross-section of sub-micron dimensions and having a length that may range from several hundreds of nanometers to several micron. The nanowire may be a solid or hollow structure, and may have a circular or non-circular, e.g. square or rectangular cross-section. The term 'nanotube' in the present application is intended to include single or multi-walled nanotubes. In a preferred embodiment, the nanowire is a silicon nanowire, which preferably has an oxidized outer surface, as will be explained in more detail later.

The substrate 110 may optionally comprise a back gate 102, e.g. a metallization layer at a surface opposite to the surface on which the buried oxide layer 120 is formed.

Figure 2:
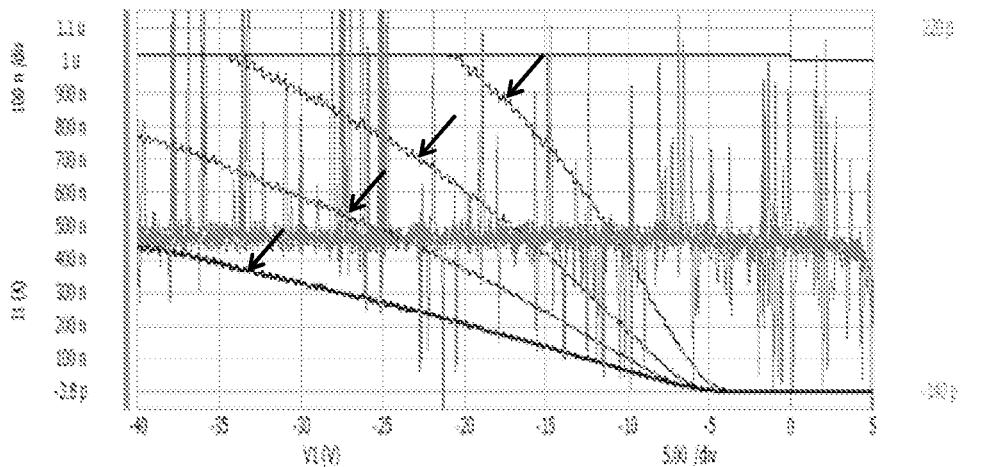
FIG. 2 depicts the current characteristics of four different nanowire sensors of an IC according to an embodiment of the present invention.

In operation, the back gate 102 is used to provide the field effect transistors 140 including the first nanowire channel region 146a and the second nanowire channel region 146b with a bias voltage waveform such that the nanowires are brought into a state of conductivity, e.g. by applying a bias voltage waveform that (at least in part) exceeds the threshold voltage of the nanowires, such that a current will start to run through the nanowires as a function of the driving current applied across the FETs formed by the source regions 142a and 142b, the first and second nanowire channel regions 146a and 146b and the common drain region 144. Because the first nanowire channel region 146a and the second nanowire channel region 146b are exposed to the medium to be measured, e.g. a fluid such as a liquid sample or a gas flow, the impedance of these channel regions is a function of the interaction of the channel region with the medium. This is demonstrated in FIG. 2, where the current characteristics of four different nanowires channel regions as indicated by the arrows are shown. The different inclinations of the current profiles are caused by different interactions with the medium, e.g. different capture event characteristics.

At this point it is noted that the drive current applied to the shared drain 144 of the array of FETs 140 may have any suitable form, e.g. a direct current or an alternating current. In case of the application of an alternating current, the impedance of the nanowires will have a complex form, i.e. comprise a real and an imaginary part. This further enhances the selectivity of a sensing FET 140, and further facilitates the detectability of materials or particles of a particular size due to the fact that the impedance will exhibit a large variation when the alternating current matches the resonance or Eigen frequency of the translational or rotational modes of the particles.

Upon returning to FIG. 1, in case of the nanowire channel regions 146a and 146b coated with an oxide film, the oxide film acts as a gate oxide with the medium acting as a gate with a floating gate potential that is dependent of the composition, e.g. ion content, of the medium. The nanowire channel regions 146a and 146b may further comprise the same or a different functional layer (not shown) for interacting with the same or a different specific analyte of interest, in which case the functional layer can be seen as the floating gate, as its potential will be a function of the amount of interaction of the functional layer with the analyte of interest. Such functional or binding layers are known per se and will not be discussed in further detail for the sake of brevity. Also, the above principles are of course known per se e.g. from ChemFETs such as ISFETs and ENFETs and will therefore not explained in further detail for reasons of brevity only.

The IC 100 further comprises a voltage waveform generator 150 conductively coupled to the back gate terminal 102 for generating a bias voltage waveform comprising a plurality of voltage pulses of alternating positive and negative value. The bias voltage waveform generated by the voltage waveform generator 150 typically is an alternating waveform, preferably but not necessarily around a zero value, in which at least one of the positive amplitudes and negative amplitudes is periodically increased. Consequently, charged particles in a medium to which the channel region 146 is exposed sense a bias voltage-induced time-averaged potential that is zero or near-zero, such that there is no effective attractive force acting on the charged particles, thus preventing the gradual contamination of the sensing surface with such charged particles. It has been surprisingly found that the application of a waveform that acts as a pulsed waveform in one of its phases substantially reduces sensor drift and dramatically increases the stability of the sensor, an effect that is not observed when a continuous or continuously increasing DC voltage is applied as a bias voltage. Moreover, such a pulsed waveform allows the determination of the I-V characteristics of the sensor.

To this end, the periodic bias voltage waveform may have a frequency that is high enough such that the charged particles are too slow to respond to a half-period of the waveform during which an attractive force is exerted on the particles of opposite charge compared to the sign of the half-period. Alternatively, at lower frequencies the charged particles may exhibit a translational pattern that is resonating with the potential generated by the applied bias voltage waveform.

In each of these scenarios, only particles that have an additional affinity with the exposed channel region, e.g. because of an additional stabilization by a specific binding event with the functional or binding layer on the channel region 146, will effectively bind to the sensing surface of the FET 140. In case of binding a charged analyte of interest to the sensing surface, care has to be taken that when applying a low-frequency periodic bias voltage waveform the repulsive potential energy does not exceed the specific binding energy of the charged analyte of interest to the binding layer of the channel region 146, such that the unwanted repulsion of the charged analyte of interest can be avoided. For a high-frequency periodic bias voltage waveform this is not a concern because the frequency is too high for the charged analyte of interest to respond to, such that the charged analyte of interest simply senses a time-averaged (near-)zero potential. Obviously, for a charge neutral analyte of interest the frequency of the applied periodic bias voltage waveform is largely irrelevant.

The IC 100 may further comprise a signal processor 160 for processing the signals produced by the FETs 140. In FIG. 1, the signal processor 160 is coupled to the individual source regions 142a, 142b of the FETs 140 for this purpose by way of non-limiting example only, as it will be readily understood by the skilled person that any suitable conductive coupling between the FETs 140 and the signal processor 160 may be applied. The signal processor 160 is adapted to derive an analyte measurement from the analyte first transistor signal acquired during said signal acquisition period, i.e. the period in which the one or more FETs 140 are enabled by the bias voltage generator 150. As the interpretation of the acquired signals is well-known per se, this will not be explained in any further detail for the sake of brevity only. In an alternative embodiment, the signal processor 160 may be omitted from the IC 100, in which case e.g. the source regions 142a, 142b may be conductively coupled to externally accessible bond pads to facilitate off-chip evaluation of the sensing signals of the FETs 140.

Figure 3:
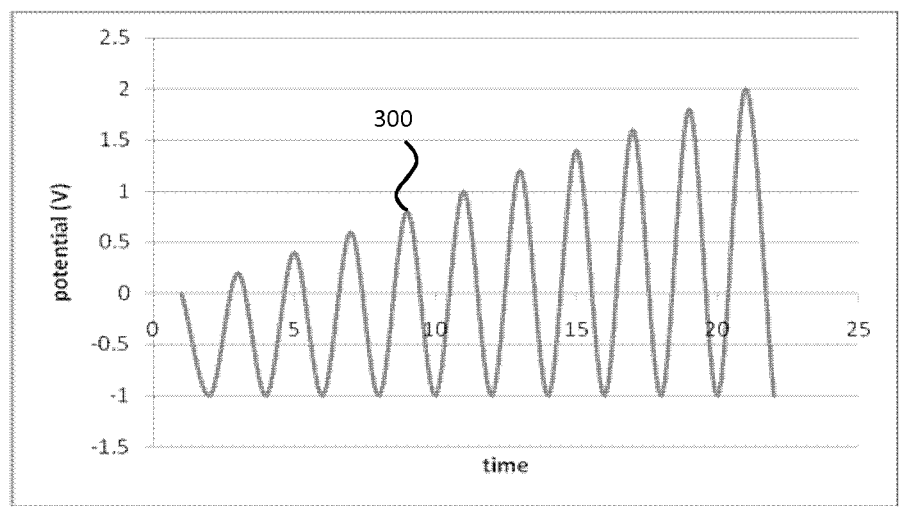
FIG. 3 depicts a bias voltage waveform according to an example embodiment of the present invention.

FIG. 3 depicts an example embodiment of a periodic bias voltage waveform 300 in which the positive amplitude is periodically increased whilst the negative amplitude is kept constant. It is noted that because the positive amplitude of the waveform starts at a value that is smaller than the negative amplitude of the waveform but periodically increases, e.g. monotonically increases, to a value larger than the negative amplitude, the time-averaged potential experienced by the charged particles is the medium still is a (near-) zero potential, thus preventing the attraction of charged particles to the sensing surface by the applied bias voltage potential, such that any binding events at the sensing surface of the FET 140 are driven by the affinity of the analyte of interest with the sensing surface.

It should be understood that the voltage waveform 300 in FIG. 3 is a non-limiting example only; other waveforms, e.g. in which the positive amplitude is kept constant and in which the negative amplitude is periodically increased, are equally feasible, as long as the time-averaged potential sensed by the charged particles in the medium is as close to zero as possible or required. Also, although the pulses in the bias voltage waveform 300 are of sinusoidal shape, it should be understood that other pulse shapes are equally feasible, e.g. block-shaped, saw tooth-shaped and so on. In a preferred embodiment, the duration of each voltage pulse, i.e. each half-period, is chosen in the range from 0.1-100 milliseconds.

Figure 4:
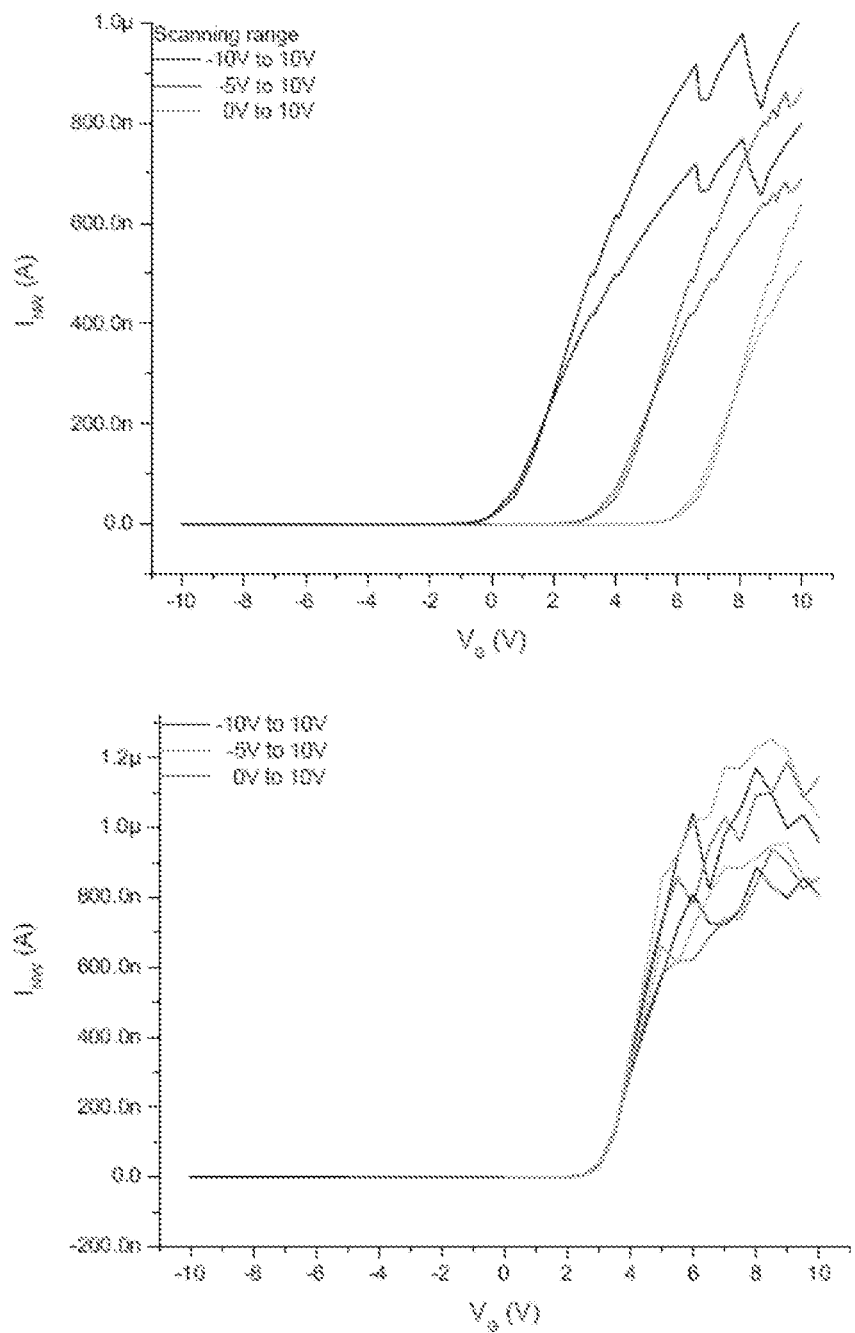
FIG. 4 depicts the response of a nanowire FET to a constant back gate voltage bias (top pane) and a back gate bias voltage waveform according to an embodiment of the present invention (bottom pane)

An additional advantage of the use of a bias voltage waveform of the present invention for biasing a sensing FET 140 as shown in FIG. 1 is demonstrated in FIG. 4. The top pane shows the response of a sensing FET to a continuously increasing voltage potential. As can be seen in the top pane, the end points of the scanning window of such a direct bias voltage influence the source-drain current characteristics and the threshold voltage $V_{th}$ of the FET 140, as demonstrated by the fact that the gate voltage at which the FET 140 becomes conductive varies. In contrast, when applying the voltage waveform of the present invention, as demonstrated in the bottom pane, the on-characteristics of the FET 140 become largely independent of the dimensions of the applied scanning window, thus improving the accuracy and robustness of the FET 140.

Figure 5:
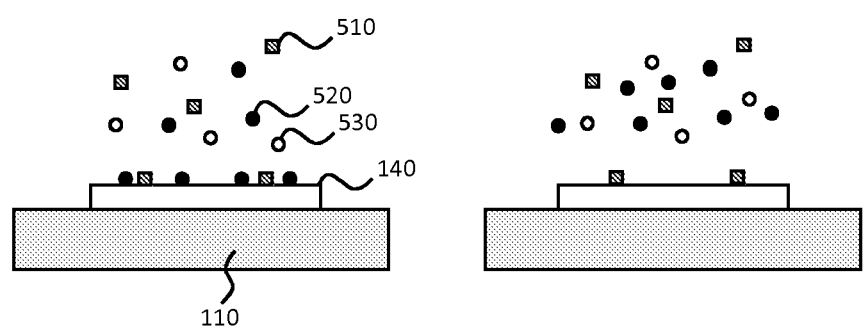
FIG. 5 depicts the accumulation behaviour at an exposed channel region of a FET biased with a constant bias voltage (left pane) and a bias voltage waveform according to an embodiment of the present invention (right pane)

FIG. 5 schematically depicts the effects of the application of a constant bias voltage during sensor signal acquisition (left hand pane) and the effect of the bias voltage waveform 300 to the FETs 140 during sensor signal acquisition (right hand pane) on the accumulation of charged contaminants at the surface of the FET 140. For a FET 140 formed on, e.g. an SOI, substrate 110 such as shown in FIG. 1, a constant bias voltage of positive sign causes a positive potential difference to exist between the exposed sensing surface of the FET 140 and the medium over the exposed sensing surface, such that negatively charged particles 520 are attracted to the exposed sensing surface in addition to the analyte of interest 510. Positively charged particles 530 are repelled from the exposed sensing surface. In contrast, when the bias voltage waveform 300 is applied to the substrate 110 acting as the back gate of the FET 140, the charged particles 520 and 530 experience a time-averaged zero potential such that the accumulation of charged particles at the exposed sensing surface is avoided, as demonstrated in the right hand pane of FIG. 5.

Figure 6:
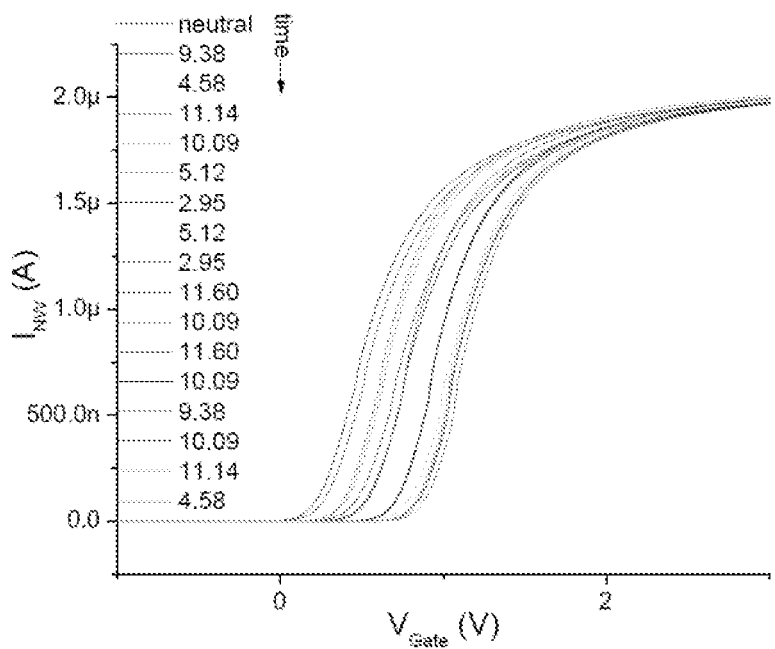
FIG. 6 depicts an experimentally obtained response from a Si-nanowire FET exposed to various NaCl solutions when biased using a back gate bias voltage waveform according to an embodiment of the present invention.

FIG. 6 are the measurement results obtained by exposing a Si-nanowire FET 140 formed in a silicon-on-insulator (SOI) substrate and functionalized as a pH sensor by covering the silicon nanowire 146 with an $Al_2O_3$ film by way of non-limiting example. Other functionalization films may of course be chosen depending on the nature of the analyte of interest. The sensor was exposed to a number of aqueous samples of different pH each comprising dissolved $Na^+$ and $Cl^-$ ions. For each pH measurement, the bias voltage waveform 300 was applied to the substrate 110 during the sensing signal acquisition phase. In each case, the pH could be accurately obtained from the sensor response, thus clearly demonstrating that the presence of $Na^+$ and $Cl^-$ ions in the solutions did not interfere with the pH measurements.

An example method of manufacturing an IC 100 is schematically depicted in FIG. 7. In step (a), a substrate 110 is provided that carries an electrically insulating layer 120 and a semiconductor material layer 130. Preferably, this arrangement is provided as a silicon on insulator substrate in which layers 110 and 130 are silicon layers separated by a buried oxide layer 120, but it should be understood that the layer stack as shown in step (a) may be provided in any suitable manner using any suitable materials. A metal contact 102 (not shown) may also be present or formed at any suitable point in the method to provide the substrate 110 with a back gate contact such that the substrate 110 can be used as a back gate.

In a next step (b), a patterned mask 710 is formed on the silicon layer 130 that defines the regions into which impurities are to be implanted, after which such impurities are implanted into the silicon layer 130, such as impurities 720, e.g. $N^-$-type impurities, in the region in which the nanowire channel regions 146 are to be formed and impurities 730, e.g. N++-type impurities, in the source and drain regions 142 and 144. As the formation of such a mask and such implantation steps are routine practice for the skilled person, they will not be explained in any further detail for the sake of brevity only.

Subsequently, the mask 710 is removed from the silicon layer 130, which is subsequently patterned to form the nanowires 146 and the source and drain regions 142 and 144, as shown in step (c). It is noted that the cross-section of the IC 100 shown in step (c) is rotated 90° compared to the cross-sections shown in step (a) and (b), such that the formed source and drain regions 142 and 144 are not shown in the cross-section of step (c). The patterning of the silicon layer 130 may be achieved in any suitable manner. Particularly preferred is the use of electron beam lithography to form the nanowires 146, which may be combined with a dry etch to form the source regions 142 and the drain region(s) 144.

Step (d) is an optional step, which is however preferred to ensure that the medium to which the nanowires 146 are exposed acts as a floating gate on the channel regions of the field effect transistors 140 including the nanowire channel regions 146. In step (d), the nanowires 146 are provided with an oxide layer 740. In case of silicon nanowires 146, this is preferably achieved by the partial oxidation of the silicon, e.g. by exposing the silicon nanowires 146 to an oxide-rich environment at elevated temperatures, e.g. 300° C. or higher for a period of time. This oxide layer 740 thus acts as a gate oxide when the nanowires 146 are brought into contact with the medium.

Next, selected nanowires 146 may be functionalized with a functionalization or binding layer 750 as shown in step (e). The one or more binding layer portions 750 may be formed in any suitable way, e.g. by deposition of a binding layer over all nanowires 146 and the selective removal of the binding layer material from those nanowires 146 that are not to be used as sensing nanowires for the analyte having affinity with the binding layer 750, or alternatively by the selective deposition of the binding layer 750 over only those nanowires 146 that are to be sensitive to the analyte of interest having affinity with the binding layer 750. Different nanowires 146 may be functionalized with different binding layers 750 as will be apparent to the skilled person. As many of such binding layer materials are well-known per se, it suffices to say that any suitable binding material may be used.

Due to the fact that the spacing between nanowires 140 is many factors larger than the cross-section or thickness of a single nanowire 140, such a selective deposition can be achieved using techniques that are routinely available to the skilled person. FIG. 8 schematically depicts a top view of a single FET 140 including source contact 842, drain contact 844, the metal 852 in conductive contact with the source contact 842 (the metal contacting the drain contact has been omitted for the sake of clarity) and the nanowire 146. This clearly demonstrates that there is ample room for the selective deposition of the binding layer 750 over the nanowire 146.

The IC 100 may be integrated in any suitable sensing apparatus. Such a sensing apparatus typically comprises a sample compartment for receiving a stationary sample of a flowing sample, in which case the sample compartment may comprise a flow channel, which may have any suitable dimensions. The IC 100 is typically placed such that the first transistors 140 are exposed in the sample compartment. Such a sensing apparatus may for instance be a microfluidics-based sensing apparatus or an assay-based sensing apparatus to be used in a healthcare application, an exhaust gas sensing apparatus to be used in a domestic, industrial or automotive application and so on. Many other suitable application domains for such a sensing apparatus will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated sensor circuit comprising:
a semiconductor substrate;
an insulating layer over said semiconductor substrate;
a first transistor on said insulating layer, said first transistor comprising an exposed channel region in between a source region and a drain region and a sensitive gate in said exposed channel region, the exposed channel region being arranged for sensing of an analyte; and
a voltage waveform generator conductively coupled to the semiconductor substrate for providing the first transistor with a bias voltage during a sensing signal acquisition period, wherein the voltage waveform generator is programmed to provide a bias voltage waveform comprising a plurality of alternating positive and negative voltage pulses, wherein only one of the positive voltage pulses and negative voltage pulses exhibits a periodically increasing amplitude and the other one of the positive voltage pulses and the negative voltage pulses remains constant.

2. The integrated sensor circuit of claim 1, further comprising a signal processor conductively coupled to the first transistor and wherein the first transistor is arranged to derive a measurement of the analyte from a signal acquired during said sensing signal acquisition period.

3. The integrated sensor circuit of claim 1, wherein the bias voltage waveform has a time-averaged zero potential, which preferably alternates around a zero value.

4. The integrated sensor circuit of claim 1, wherein the exposed channel region is selected from a group consisting of: a nanowire and a nanotube.

5. The integrated sensor circuit of claim 4, wherein the nanowire comprises a silicon nanowire.

6. The integrated sensor circuit of claim 4, wherein the nanotube comprises a carbon nanotube.

7. The integrated sensor circuit of claim 1, wherein the channel region is covered by an oxide layer.

8. The integrated sensor circuit of claim 1, wherein the first transistor is part of a plurality of first transistors.

9. A sensing apparatus comprising: a sample compartment; and an integrated sensor circuit comprising: a semiconductor substrate; an insulating layer over said semiconductor substrate; a first transistor on said insulating layer, said first transistor comprising an exposed channel region in between a source region and a drain region and a sensitive gate in said exposed channel region, the exposed channel region being arranged for sensing of an analyte; and a voltage waveform generator conductively coupled to the semiconductor substrate for providing the first transistor with a bias voltage during a sensing signal acquisition period, wherein the voltage waveform generator is programmed to provide a bias voltage waveform comprising a plurality of alternating positive and negative voltage pulses, wherein only one of the positive voltage pulses and negative voltage pulses exhibits a periodically increasing amplitude and the other one of the positive voltage pulses and the negative voltage pulses remains constant, wherein the first transistor is exposed to said sample compartment.

10. The sensing apparatus of claim 9, wherein said sample compartment comprises a flow channel.

11. A method of measuring an analyte of interest in a medium, the method comprising: providing an integrated sensor circuit comprising: a semiconductor substrate; an insulating layer over said semiconductor substrate; a first transistor on said insulating layer, said first transistor comprising an exposed channel region in between a source region and a drain region and a sensitive gate in said exposed channel region, the exposed channel region being arranged for sensing of an analyte; and a voltage waveform generator conductively coupled to the semiconductor substrate for providing the first transistor with a bias voltage during a sensing signal acquisition period, wherein the voltage waveform generator is programmed to provide a bias voltage waveform comprising a plurality of alternating positive and negative voltage pulses, wherein only one of the positive voltage pulses and negative voltage pulses exhibits a periodically increasing amplitude and the other one of the positive voltage pulses and the negative voltage pulses remains constant; exposing the first transistor to a medium potentially including an analyte to be sensed with the first transistor; and deriving an analyte measurement from a signal acquired during said sensing signal acquisition period.

12. The method of claim 11, wherein the bias voltage waveform has a time-averaged zero potential.

13. The method of claim 11, wherein the bias voltage waveform alternates around a zero value.

* * * * *